United States Patent [19]

Schuette et al.

[11] 4,106,492
[45] Aug. 15, 1978

[54] REAL TIME TWO-DIMENSIONAL MECHANICAL ULTRASONIC SECTOR SCANNER WITH ELECTRONIC CONTROL OF SECTOR WIDTH

[75] Inventors: William H. Schuette, McLean, Va.; George F. Norris, Kensington, Md.

[73] Assignee: The United States of America as represented by the Secretary of the Department of Health, Education and Welfare, Washington, D.C.

[21] Appl. No.: 758,851

[22] Filed: Jan. 12, 1977

[51] Int. Cl.² .............................................. A61B 5/00
[52] U.S. Cl. ............................... 128/2 V; 128/2.05 Z; 73/619
[58] Field of Search ............... 128/2 V, 2.05 Z, 24 A; 343/7 A, 5 MM; 340/3 C; 358/285, 111, 112; 73/67.8 R, 67.8 S, 619

[56] References Cited

U.S. PATENT DOCUMENTS

| | | | |
|---|---|---|---|
| 3,086,390 | 4/1963 | Brown | 73/67.8 S |
| 3,096,444 | 7/1963 | Seward | 250/231 R X |
| 3,403,671 | 10/1968 | Flaharty | 128/2 V |
| 3,406,564 | 10/1968 | Phillips et al. | 73/67.8 S |
| 3,447,052 | 5/1969 | Martin et al. | 310/3 C X |
| 3,482,106 | 12/1969 | Anderegg et al. | 250/231 R |
| 3,654,479 | 4/1972 | Catherin | 250/231 SE |
| 3,775,617 | 11/1973 | Dubauskas | 250/231 R X |
| 3,927,661 | 12/1975 | Takemura | 128/24 A X |
| 4,034,744 | 7/1977 | Goldberg | 128/2V |

OTHER PUBLICATIONS

Griffith, "A Sector Scanner for Real-Time Two Dimensional Echo-Cardiography," Circulation vol. 49, Jun. 1974, pp. 1147-1152.
McDicken, W. N. et al., "An Ultrasonic Instrument for Rapid B-Scanning of the Heart," Ultrasonics Viz. #6, Nov. 1974, pp. 269-271.
Nakashika, M. et al., "Recent Ultrasonic Tomographic System-Sono-layer graph SSL-31A," Toshiba Review, No. 82, Jun. 1973, pp. 13-18.

Primary Examiner—Robert W. Michell
Assistant Examiner—Francis J. Jaworski
Attorney, Agent, or Firm—Browdy and Neimark

[57] ABSTRACT

An ultrasonic scanning system for echocardiography or the like, the system including a pivoted transducer in a manually-held housing containing a reversible low-inertia servo motor drivingly connected to the transducer via reduction gearing for oscillating the transducer, and a photoelectric system for generating sine and cosine voltages representing the real time positions of the transducer. An electronic position control circuit controls the motor, and thus controls the position of the transducer, by feedback signals derived from the difference between the sine function generated in the photoelectric system and a triangular wave generated in the control circuit. This difference is used to determine the magnitude and polarity of the voltage applied to the servo motor. This makes it possible to program the sector position of the transducer as a function of time. The photoelectric system may consist of a slotted disc mounted on the motor shaft between light sources and arrays of photocells. The disc has respective slots arranged to permit light proportionate to the sine and cosine of the sector position angle of the transducer to pass through the disc to the photocell arrays. The generated sine and cosine voltages are used to derive X and Y sweep voltages for an associated cathode ray tube display.

10 Claims, 6 Drawing Figures

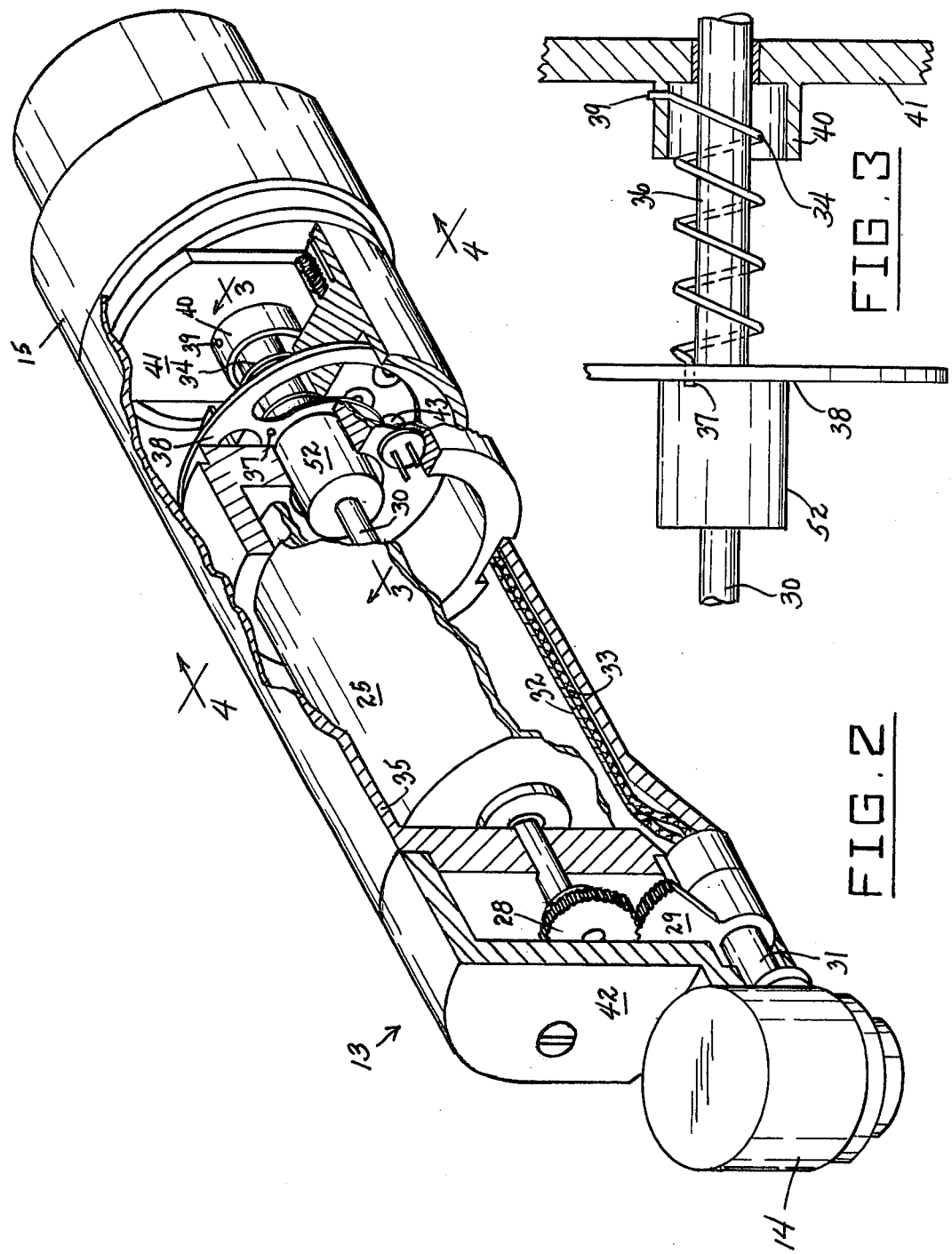

REAL TIME TWO-DIMENSIONAL MECHANICAL ULTRASONIC SECTOR SCANNER WITH ELECTRONIC CONTROL OF SECTOR WIDTH

FIELD OF THE INVENTION

This invention relates to medical instruments for observing organs of the body, and more particularly to a two-dimensional ultrasonic pulse echo scanning system for performing real time two-dimensional echocardiography or similar applications of pulse echo ultrasonic technique.

BACKGROUND OF THE INVENTION

During recent years one-dimensional pulse echo ultrasonic techniques have proven to be extremely useful in cardiac diagnosis. A one-dimensional system, however, only measures distances to structures lying along a single straight line. Cardiac anatomy is therefore not so easily defined as with a two-dimensional system which simultaneously measures distances along many straight lines comprising a plane. Several systems have been described for obtaining two-dimensional echo cardiograms. None, however, has combined electronic control of sector width and scan linearity with the advantages of a high sensitivity, narrow beam transducer, real time imaging, and a simple method for controlling the section of the heart being viewed. A serious limitation of the presently available electro-mechanical sector scanners is the lack of electronic control of sector width and scan linearity.

In the course of a preliminary search, the best prior art found relating to the subject matter of the present invention appears to comprise the following U.S. Pat. Nos.

Eggleton et al, 3,817,089
Lee at al, 3,893,449
Ranalli et al, 3,864,668
Wilcox, 3,881,466
Takemura, 3,927,661
Kossoff, 3,939,696
Eggleton, 3,955,561
Eggleton et al, 3,974,826

The following publications also appear to represent the known state of the art:

Fiegenbaum, "Clinical Applications of Echocardiography, Prog. Cardiovase Dis.," 14: 531, 1972.

Popp and Harrison, "Ultrasound in the Diagnosis and Evaluation of Therapy of Idiopathic Hypertrophic Subaortic Stenosis," Circulation, 40: 905, 1969.

Henry and Epstein, "Aymmetric Septal Hypertrophy ; Echocardiographic Identification of Pathognomic Anatomic Abnormality of IHSS," Circulation, 47: 225, 1973.

Griffith and Henry, "A Sector Scanner for Real Time Two-dimensional Echocardiography," Circulation 49: 1147, 1974.

Flaherty, Clark and Walgren, "Simultaneous Fluoroscopic and Rapid Scan Ultrasonic Imaging," Dig. Int. Conf. Med. Biol. Eng., 7; 221, 1967.

Thurston and Von Ramm, "A New Ultrasound Technique Employing Two-Dimensional Electronic Beam Steering," in Acoustical Holography, Vol, 5, Plenum Publishing Corp., New York, 1974.

Perhaps the most pertinent of the prior systems is that disclosed by Griffith et al; however this prior system does not provide a sufficient linear sector sweep and thus requires the use of small sector angles. Accordingly, the need exists for a system of the type desired below.

SUMMARY OF THE INVENTION

It is, accordingly, an object of the present invention to overcome the deficiencies of the prior art, such as indicated above.

It is a further object to provide for improved visualization of hidden members by means of ultrasonic scanning.

Another object of the present invention is to provide a novel and improved hand-held electro-mechanical ultrasonic scanner employing electronic position feedback control so that a linear scan can be obtained, as well as electronic control of sector width.

A further object of the invention is to provide an improved electro-mechanical ultrasonic scanner of the pulse echo type which has sector sweep means of highly improved linearity, making it possible to employ larger sector angles than have been previously attainable, and which has continuously variable electronically controlled sector width capability.

A still further object of the invention is to provide an improved mechanical real-time ultrasonic sector scanner for use in medical diagnosis and which utilizes electronic position control of its transducer and means for electronically programming scan linearity and sector width, the scanner including a servo motor gearingly coupled to the transducer and counterbalancing the transducer rotational inertia, thereby reducing the mechanical vibration of the system, employing photoelectrically generated voltages required for display purposes, employing torsion spring means connected between the motor shaft and the scanner housing to provide an approach to system resonance and thereby reduce the electrical power consumption, and having means to utilize one of the photoelectrically generated voltages as a position signal for feedback control.

BRIEF DESCRIPTION OF THE DRAWINGS

Further objects and advantages of the invention will become apparent from the following description and claims, and from the accompanying drawings, wherein:

FIG. 2 is an enlarged perspective view, with parts broken away, of the hand-held scanner employed in the system of FIG. 1.

FIG. 3 is an enlarged fragmentary vertical cross-sectional view taken substantially on the line 3—3 of FIG. 2, showing the resonance torsion spring.

DESCRIPTION OF A PREFERRED EMBODIMENT

A main feature of the scanner system of the present invention is its applicability for use in two-dimensional echocardiography, which is an extremely useful technique, particularly in the study of acquired heart disease. The mechanical scanning of a single ultrasonic transducer permits the utilization of existing one-dimensional ultrasonic equipment to generate two-dimensional ultrasonic images that are required for echocardiography. One limitation of the presently available electro-mechanical sector scanners is the lack of electronic control of sector width and scan linearity (uniform line density). This system limitation occurs as a result of obtaining the scanning motion through the use of an eccentric gear in conjunction with a constant speed motor*.

*Griffith and Henry, "A Sector Scanner for Real Time Two-Dimensional Echocardiography," Circulation 49: 1147, 1974

Fortunately, the rotational inertia of the ultrasonic transducer assembly is low enough to permit the design of a position-sensitive feedback control system for scanning purposes. As a direct result of position feedback control, sector width and scan linearity may be programmed, and this is a primary feature of the present invention.

In the typical system according to the present invention herein described, a single ultrasonic transducer, such as Aerotech 2.25 MHz, is moved through an angle that is programmable from 0° to ± 25°. The sector scan rate is variable from 0 to 40 scans per second, and scan linearity is achieved by electronic programming of the transducer position to match that of a triangle waveform.

Figure 1:
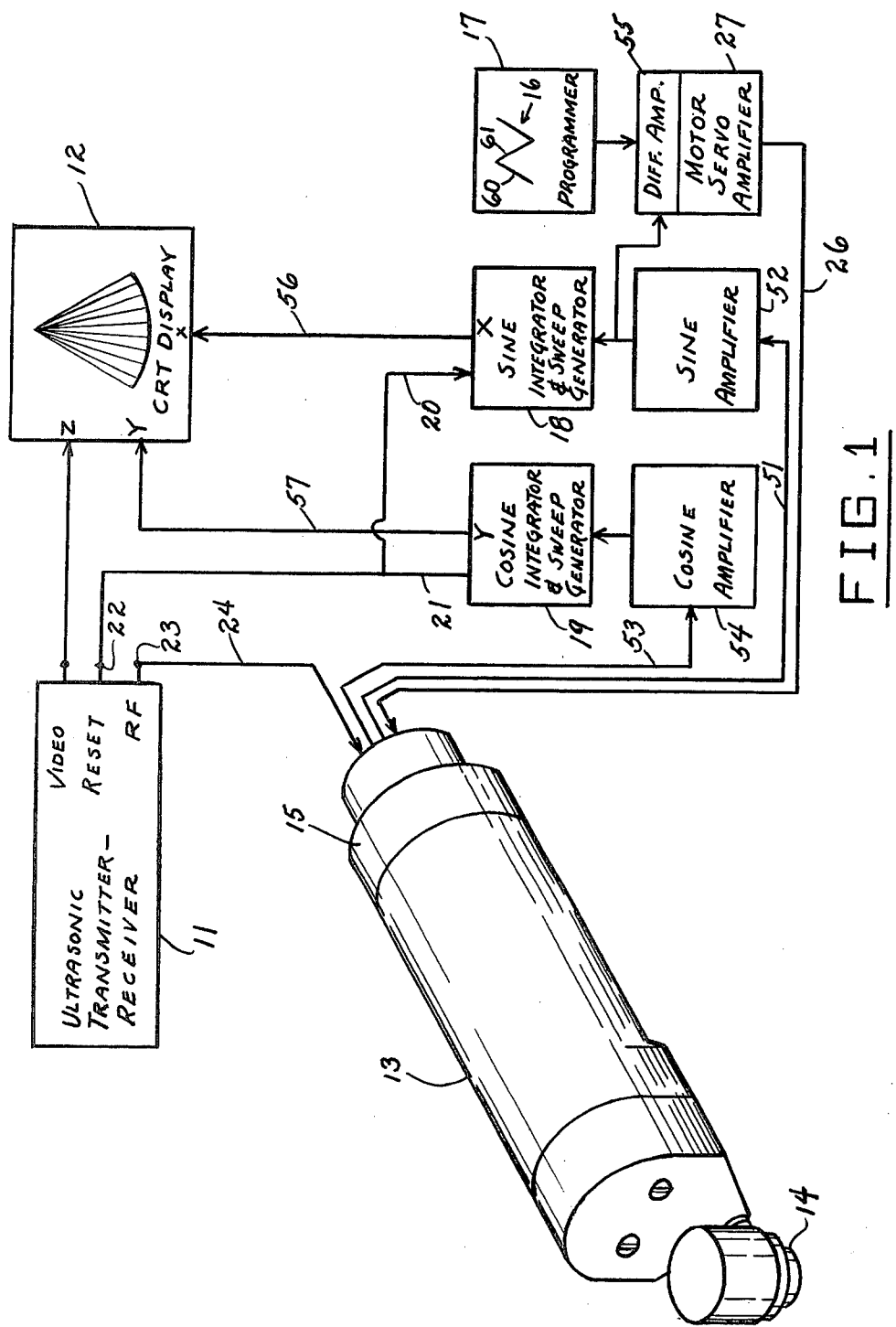
FIG. 1 is a block diagram of a complete two-dimensional ultrasonic echographic system according to the present invention.

At scan rates above 20 scans per second, however, the scanner position function approaches a sinusoid due to mechanical resonance of the system. A block diagram of the complete two-dimensional ultrasonic echographic system is shown in FIG. 1. The major components of the system are an ultrasonic transmitter-receiver 11, which may be similar to Ekoline 20A,* a cathode ray tube display assembly 12, such as Tektronic 453, and a hand-held scanner 13, with accompanying electronics for position control of the transducer unit 14 and generation of sweep voltages for the X and Y axes of the CRT display device 12. The position of the transducer unit 14 relative to the body of scanner 13 is controlled by feedback to the scanner servo motor, shown at 15. This feedback consists of a voltage proportional to the difference between the sine of the transducer unit position angle and the value of the triangle wave form 16 from a triangle waveform programmer 17.** The X and Y sweep voltages required for the CRT display are generated by integrating the sine and associated cosine voltages and resetting the integrators, shown at 18, 19, via reset lines 20, 21 from the reset output terminal 22 of transmitter-receiver 11, with each transmitted pulse. The transducer driving pulses are delivered to the transducer crystal in unit 14 from the RF output terminal 23 of transmitter-receiver 11 via a line 24, which also carries the echo pulses.

*Manufactured by Smith Kline Instrument Company, Palo Alto, Calif.
**Similar to Wavetek Function Generator, manufactured by Wavetek, Inc.

The transducer unit 14 is driven by servo motor 15, which is a high-performance, low-inertia DC motor, similar to Micro Switch, 26 EM series. This motor incorporates a hollow-rotor armature 25 yielding both low inertia and low inductance. Thus, the armature can be quickly started and stopped without difficulty and can be made to follow accurately the rapid servo signals delivered thereto via a line 26 from a motor servo amplifier 27.

The motor 15 is reversed for each scan in accordance with the driving triangular programmer wave 16, which has linear forward and reverse sections 60, 61. Said motor 15 is gearingly coupled at a 3 : 1 speed ratio to the transducer unit 14 by a pinion gear 28 on the motor shaft and a sector gear 29 on the hollow shaft 31 of the unit 14. Thus, the torque from the motor is multiplied by 3 in being applied to the transducer unit 14. The use of a single gear reduction results in the motor shaft 30 and the transducer unit 14 rotating in opposite directions. This permits the cancellation of the rotational inertia of the transducer unit 14 by that of the motor 15, thus minimizing mechanical vibration. The transducer wires 32, 33 extend through the center of the hollow sector gear shaft 31 so that angular vibration imparted to the wires is distributed over a length of the order of 4 cm. Consequently, the wires are less vulnerable to breakage. Power consumption at high scan speeds is minimized by the use of a torsion spring 34 (see FIG. 3) connected between the motor shaft and the scanner housing 35. As shown in FIG. 3, the torsion spring 34 surrounds a thickened portion 36 of the motor shaft, one end of the spring being anchored at 37 to a sine-cosine function disc 38 rigidly secured on another thickened portion 52 of the shaft, and the other end being anchored at 39 to a sleeve element 40 concentric with the shaft and integral with a shaft bearing bracket 41 fixed to housing 35. Spring 34 assists motor reversal.

Torque spring 34 may be omitted where power consumption is not an important factor.

Mechanical stops, not shown, may be provided on the end wall 42 of the scanner housing, arranged to be engaged by the side edges of sector gear 29 to limit the angular movement of the transducer unit 14 to ± 25°, and consequently to limit the angular movement of the motor armature to 150° of rotation.

Figure 5:
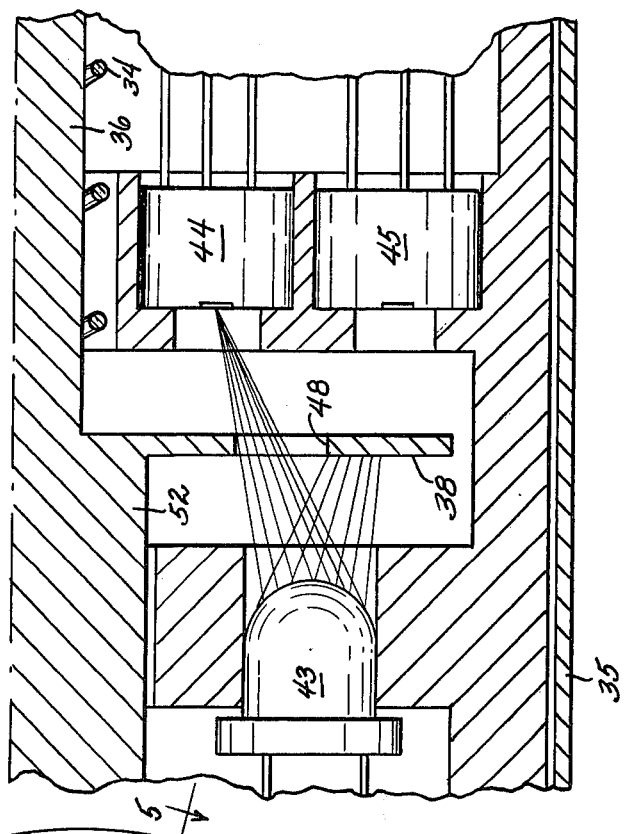
FIG. 5 is an enlarged fragmentary cross-sectional view taken substantially on line 5—5 of FIG. 4.
Figure 4:
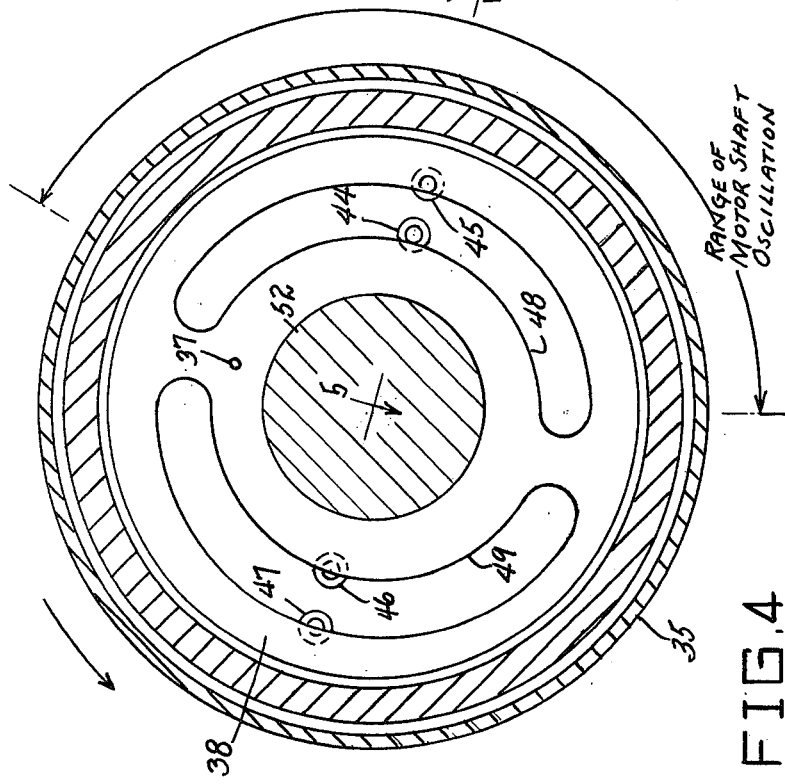
FIG. 4 is an enlarged transverse vertical cross-sectional view taken substantially on line 4—4 of FIG. 2.

The angular position of the transducer unit 14 is detected photoelectrically by means of the sine-cosine function disc 38 mounted on the motor shaft, in cooperation with respective light-emitting diodes 43 with translucent lenses, mounted in the scanner housing at one side of the disc 38, and respective photocell arrays 44, 45 and 46, 47 mounted in the scanner housing at the opposite side of disc 38, as shown in FIGS. 4 and 5. Respectively generally arcuate constant-width slots 48 and 49 are formed in opposite portions of disc 38 and are arranged, in cooperation with said photocell arrays, to generate signals providing respective sine and cosine functions of the transducer angle. Thus, slot 48 is oriented so that its side edges form variable schlieren edges with respect to the rays from the adjacent light source 43, changing in amoung of overlap of the associated photocells 44, 45 with angular movement of disc 38. Photocells 44, 45 are of the photovoltaic type and generate voltage signals in accordance with the amounts of light flux received thereby. The voltage signals are subtracted one from the other in an associated differential amplifier 50. The slot 48 is shaped and oriented so that the resultant output at 51 is a sine function of the transducer angle. As the function disc 38 rotates, the slot 48 moves relative to the photocell array 44, 45, controlling the amount of light flux reaching the photocells to thereby generate said sine function.

Figure 6:
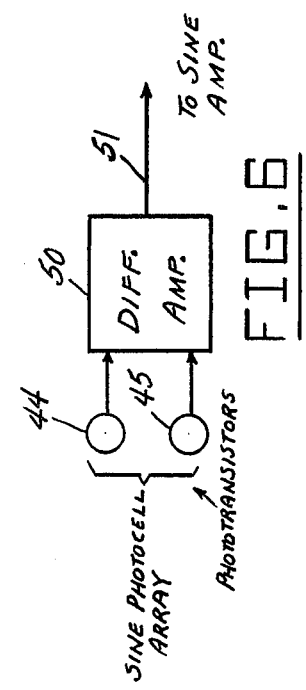
FIG. 6 is a block diagram showing the connections of a pair of photocells to a differential amplifier to derive a resultant difference signal, as employed in the scanner system of FIGS. 1 to 5.

The opposite slot 49 is shaped and oriented to generate the cosine function of the transducer angle in cooperation with another light source and the photocell array 46, 47 whose output voltages are subtracted one from the other by another differential amplifier 50 connected in a manner similar to that shown in FIG. 6.

As will be seen from FIGS. 4 and 5, as the transducer unit 14 rotates, the relative amounts of light flux received by the photocell pairs 44, 45 and 46, 47 through the constant-width slots 48, 49 change, and differential amplification of the respective pairs of detector outputs provide sine and cosine function signals with respect to the transducer angle.

The constant-width generally arcuate slots 48, 49 are not concentric with the disc 38 and are carefully shaped to yield the desired sine and cosine functions. As an alternative, the slot 49 and associated light source 43 and photocells 46, 47 may be omitted, and the cosine function may be derived electronically from the generated sine function by the use of suitable computing circuitry well known in the art.*

*See U.S. Pat. No. 3,955,561

As shown in FIG. 1, the sine function output voltage in line 51 is supplied to the input of a sine amplifier 52 and the cosine function output voltage is supplied via a line 53 to the input of a cosine amplifier 54.

At its output, sine amplifier 52 provides a signal representing the angular position of the transducer unit 14. This signal is compared in a differential amplifier 55 with the guiding triangle wave signal 16, and the resultant difference signal is applied as an input to the motor servo amplifier 27. The amplified feedback positional correction signal at the output of amplifier 27 is applied to the servo motor 15 via line 26. Since said feedback correction signal consists of a voltage proportional to the difference between the actual transducer position (sine of the transducer position angle) and that corresponding to scan linearity (a concurrent point along the triangle wave 16) the movement of the rotating armature of the servo motor 15 is automatically corrected to provide transducer scan linearity. Also, the programmer 17 can be adjusted to vary the length of the triangle waves 16, thus providing control of sector width, and enabling the sector size to be adjusted from 0° to about ±25°. Also, the scan rate can be adjusted from 0 to about 40 scans per second by adjusting the frequency of the triangle waves 16.

The X and Y sweep voltages required for the CRT display are generated by integrating the sine and cosine voltages in the integrator-sweep generator stages 18 and 19 and resetting the integrators with each transmitted pulse. The X and Y sweep voltages are furnished to the CRT unit 12 via lines 56 and 57.

The angular coverage of the sine voltage generated by the slot 48 is preferably made somewhat greater than that corresponding to the ±25° mechanical limits of transducer scanning oscillation to prevent electronic lock up of the system. The generation of accurate sine and cosine voltages may be simplified by substantially matching the dynamic coverage of the sine-cosine function disc 38 to the mechanical limits of the scanner and also by inserting a DC component for the cosine function at the Y axis integrator.

In operation, the apparatus may be employed to obtain planar cross-sections of an organ, for example, a heart, by applying the hand-held scanner 13 to a suitable selected position of the patient's chest. The examination is done in real time, using the hand-held scanner while the operator watches the video display on the CRT unit 12 and simultaneously adjusts the scanner position until the heart section to be viewed is displayed. The section can be chosen at any orientation relative to the heart's major and minor axes. If so desired, the video display may be recorded for later study by the use of a suitable motion picture camera or a video tape recorder with an associated video camera.

While a specific embodiment of an improved real time ultrasonic scanning apparatus for medical examination of the body has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiments.

What is claimed is:

1. A real time ultrasonic scanning apparatus for medical examination of the body, the apparatus comprising hand-held housing means provided with a pivoted transducer and a reversible servo motor drivingly connected to said transducer, means for generating a positional electrical signal function varying in accordance with the angular position of said transducer over a scanning range of oscillation, programming means for generating periodic substantially triangular control wave signals including linear forward and reverse sections, position feedback control means for energizing said servo motor in accordance with the difference between the values of the position signal function and the triangular signals over the scanning range of oscillation of said transducer, pulse scan display means, means operatively connecting said transducer to said display means, and means for synchronizing said pulse scan display means with said positional electrical signal function.

2. The scanning apparatus of claim 1, and wherein said pulse scan display means comprises cathode ray tube display means operatively connected to the transducer to display pulse reflections and having beam sweep means to form a raster, and wherein said synchronizing means comprises means operatively coupling said positional signal function to said beam sweep means.

3. The scanning apparatus of claim 2, and wherein said positional signal function is substantially sinusoidal.

4. The scanning apparatus of claim 1, and wherein said housing means comprises an elongated housing adapted to be hand held and wherein said transducer is pivoted to an end portion of the housing.

5. The scanning apparatus of claim 4, and wherein said transducer is gearingly coupled to said servo motor.

6. The scanning apparatus of claim 5, and wherein said transducer is provided with a first gear element and said motor has a shaft provided with a second gear element meshing with the first gear element and providing a single gear reduction wherein the motor shaft and the transducer rotate in opposite directions, permitting cancellation of the rotational inertia of the transducer by that of the motor.

7. The scanning apparatus of claim 1, and wherein said positional function generating means comprises a slotted member drivingly connected to said motor, stationary illuminating means and photosensitive means mounted on opposite sides of said slotted member, said slotted member having a slot in the light path between said illuminating means and photosensitive means formed to cause said photosensitive means to generate said positional signal function.

8. The scanning apparatus of claim 7, and wherein said photosensitive means comprises respective photocells adjacent opposite edges of said slot, and means differentially combining the outputs of said photocells to derive said positional signal function.

9. The scanning apparatus of claim 7, and wherein said slotted member has an additional slot, and wherein additional stationary illuminating means and photosensitive means are provided on opposite sides of the slotted member with said additional slot being located in the light path between said additional illuminating means and photosensitive means, and wherein said additional slot is formed to generate another positional signal function related to said first-named positional signal function.

10. The scanning apparatus of claim 1, and torsion spring means connected between said motor and said housing means to assist the motor to reverse.

* * * * *